(12) United States Patent
Dakin

(10) Patent No.: US 10,188,676 B2
(45) Date of Patent: Jan. 29, 2019

(54) ANTI-INFLAMMATORY SOLUTION

(71) Applicant: Hypo-Stream Limited, Melbourn (GB)

(72) Inventor: Myles H. E. Dakin, Cambourne (GB)

(73) Assignee: Hypo-Stream Limited, Melbourn (GB)

( * ) Notice: Subject to any disclaimer, the term of this patent is extended or adjusted under 35 U.S.C. 154(b) by 0 days.

(21) Appl. No.: 15/450,245

(22) Filed: Mar. 6, 2017

(65) Prior Publication Data

US 2017/0266226 A1 Sep. 21, 2017

Related U.S. Application Data

(63) Continuation of application No. 14/526,762, filed on Oct. 29, 2014, now abandoned.

(60) Provisional application No. 61/896,976, filed on Oct. 29, 2013.

(30) Foreign Application Priority Data

Oct. 29, 2013 (GB) .................................. 1319109.3
Jan. 23, 2014 (GB) .................................. 1401124.1

(51) Int. Cl.
| | | |
|---|---|---|
| *A61K 8/20* | (2006.01) | |
| *A61K 9/00* | (2006.01) | |
| *A61K 9/08* | (2006.01) | |
| *A61K 33/14* | (2006.01) | |
| *A61K 33/20* | (2006.01) | |
| *A61Q 11/00* | (2006.01) | |
| *A61Q 19/00* | (2006.01) | |

(52) U.S. Cl.
CPC ................ *A61K 33/20* (2013.01); *A61K 8/20* (2013.01); *A61K 9/0014* (2013.01); *A61K 9/08* (2013.01); *A61K 33/14* (2013.01); *A61Q 11/00* (2013.01); *A61Q 19/005* (2013.01)

(58) Field of Classification Search
CPC ...................................................... A61N 1/30
See application file for complete search history.

(56) References Cited

U.S. PATENT DOCUMENTS

| | | | |
|---|---|---|---|
| 5,855,922 A | 1/1999 | Danner et al. | |
| 7,393,522 B2 * | 7/2008 | Najafi | A01N 59/00 424/613 |
| 9,072,726 B2 | 7/2015 | Alimi et al. | |
| 2002/0114851 A1 | 8/2002 | Camper et al. | |
| 2004/0232381 A1 | 11/2004 | Pinza et al. | |
| 2010/0112680 A1 | 5/2010 | Brockwell et al. | |
| 2010/0284951 A1 | 11/2010 | Pongprapansiri et al. | |
| 2013/0209442 A1 | 8/2013 | Novoa | |
| 2015/0118325 A1 | 4/2015 | Dakin | |

FOREIGN PATENT DOCUMENTS

| | | |
|---|---|---|
| GB | 1418193 A | 12/1975 |
| JP | 2007-517064 A | 6/2007 |
| JP | 2008-534516 A | 8/2008 |
| RU | 2229864 C1 | 6/2004 |
| RU | 2320329 C1 | 3/2008 |
| WO | 2005/065383 A2 | 7/2005 |
| WO | 2006/102680 A2 | 9/2006 |
| WO | WO-2010/148004 A1 | 12/2010 |
| WO | WO-2011/128682 A2 | 10/2011 |
| WO | WO-2012/123695 A2 | 9/2012 |
| WO | WO-2012/142407 A1 | 10/2012 |
| WO | 2013/116773 A1 | 8/2013 |
| WO | WO-2014/016157 A1 | 1/2014 |

OTHER PUBLICATIONS

Coetzee et al., "The use of topical, un buffered sodium hypochlorite in the management of burn wound infection." Burns 38 (2012) 529-533.*
Kebir et al., "Role of Neutorphil Apoptosis in the Resolution of Inflammation." TheScientificWorldJournal (2010) 10, 1731-1748.*
Pelgrift et al., "Topical Hypochlorous acid (HOCl) as a Potential Treatment of Pruritus." Curr Derm Rep (2013) 2:181-190. (Year: 2013).*
Dakin's "Full Strength Solution"®, Century Pharmaceuticals, Inc., retrieved from internet Jan. 30, 2015, URL: http://www.dakins.net/index.html (2011).
Danilkov et al., "The effect of indirect electrochemical oxidation with solution of sodium hypochlorite on inflammation in the kidneys and urinary tract," *Urologiya i Nefrologiya*, 0(3):25-27 (1998) (Russian language with English abstract).
De Nardo et al., "Effects of 0.05% sodium hypochlorite oral rinse on supragingival biofilm and gingival inflammation," *Int. Dental J.*, 62(4):208-212 (2012).
El Kebir and Filep, "Role of Neutrophil Apoptosis in the Resolution of Inflammation," *Sci. World J.*, 10:1731-1748 (2010).
English abstract of RU 2229864 C1.
English abstract of RU 2320329 C1.
Leung et al., "Topical hypochlorite ameliorates NF-κB-mediated skin diseases in mice," *J. Clin. Invest.*, 123(12):5361-5370 (2013).
Lindfors, "A Comparison of an Antimicrobial Wound Cleanser to Normal Saline in Reduction of Bioburden and its Effect on Wound Healing," *Ostomy/Wound Management*, 50(8):28-47 (2004).
UK Search Report for GB 1319109.3, dispatched Apr. 29, 2014.
Wong et al., "Efficacy and safety of sodium hypochlorite (bleach) baths in patients with moderate to severe atopic dermatitis in Malaysia," *J. Dermatol.*, 40(11):874-880 (2013.

\* cited by examiner

*Primary Examiner* — Walter E Webb
(74) *Attorney, Agent, or Firm* — McCarter & English, LLP; Yu Lu

(57) ABSTRACT

The present invention provides a method for preventing or treating an inflammatory response, condition or disease in a mammal comprising administering an effective amount of a dilute stabilised hypochlorite solution to said mammal in need thereof as well as a means for mixing and administering fresh, dilute stabilised hypochlorite solution to the site where it is needed.

14 Claims, No Drawings

ANTI-INFLAMMATORY SOLUTION

REFERENCE TO RELATED APPLICATIONS

This application is a continuation application of U.S. Ser. No. 14/526,762, filed on Oct. 29, 2014, which claims the benefit of the filing date under 35 U.S.C. § 119(e) to U.S. Provisional Application No. 61/896,976, filed on Oct. 29, 2013. This application also claims foreign priority to GB application no. 1319109.3, filed on Oct. 29, 2013; and to GB application no. 1401124.1, filed on Jan. 23, 2014. The entire contents of each of the above-referenced applications are incorporated herein by reference.

FIELD OF THE INVENTION

The present invention concerns a new approach to the prevention and treatment of inflammation in a mammal, especially a human, e.g., in the prevention or treatment of an inflammatory response in uncontaminated or non-infected surgical sites, wounds, trauma sites, internal inflammatory lesions or surface inflammatory lesions where there is no infection, such as in leg ulcers or other venous ulcers, or in the prevention or treatment of an inflammatory skin condition such as mouth ulcers, eczema or psoriasis.

BACKGROUND TO THE INVENTION

Many relatively simple surgical interventions still carry a significant risk of failure to heal or infection. Prevalence surveys suggest that approximately 8% of UK hospital patients have a healthcare-associated infection, with surgical site infections (SSIs) accounting for up to 20% of these (Plowman et al., *J. Hospital Infection.*, 2001, 47:198-209). Nearly 5% of patients who had undergone a surgical procedure were found to have developed an SSI, with over one third of post-operative deaths resulting at least partly from SSIs. The cost of infection is significant, with an estimated 1-2 weeks' extra hospitalization for infected patients, a doubling of re-admission rates, and a tripling of overall healthcare costs.

Fournel et al., *Brit. J. Surg.*, 2010, 97:1603-1613 published a meta-analysis of non-infected surgical sites, which underwent routine surgery with the benefit of gold standard aseptic surgical technique in pan-European centres. It was reported in this paper that surgical site infections were ubiquitous following routine and trauma surgery. Surgical site infection rates of 14% were the norm in the UK and France, whereas in Finland published figures suggest rates of up to 29% are commonplace. Surgical site infection rates of up to 40% have been reported for other countries.

The Fournel meta-analysis looked at the use of wound washes and found that four types were used during elective and trauma surgery:
1. Saline
2. Saline with bacitracin (a topical antibiotic)
3. Saline with chlorhexidine and povidone-iodine
4. Chlorhexidine povidone-iodine The current opinion among surgeons is that povidone-iodine application as a wound wash is beneficial and reduces rates of surgical site infection. Although the meta-analysis showed a statistically significant difference in surgical site infection rates when using povidone-iodine, the reduction observed was only from 14% to 8%.

Furthermore, generalised and local oedema (swelling) is frequently observed following major and simple surgery. This oedema is a product of inflammation, which originates at the surgical site, in part, as a result of the cytokine response to surgical injury. The oedema and inflammation is associated with clinical outcome, morbidity and mortality, such that a reduction in post-surgical inflammation and oedema would result in improved outcomes (Vaughan-Shaw et al., *Ann. R. Coll. Surg. Eng.*, 2013, 95:390-396). In the Vaughan-Shaw (2013) study, death was more likely in those with post-operative oedema (47% vs 8%).

Furthermore, it is believed that specific proteins and molecules act as inflammatory mediators in the contribution to rheumatoid diseases (Montecucco et al., "Common Inflammatory mediators orchestrate pathophysiological processes in rheumatoid and arthritis," *Rheumatology*, 2009, 48:11-22) as well as Alzheimer's degenerative disorders of the nervous system (Akiyama et al. Inflammation and Alzheimer's disease. Neurobiology of aging. 2000; 21:383-421). The ability to modify or attenuate the bio-activity of these mediators would impact the progression of these diseases.

A dental extraction/oral surgical procedure is analogous to the intentional creation of a compound fracture in the oral cavity, where the wound is left to heal by secondary intention. Although osteomyelitis (infection) is rare after any oral and maxillofacial surgery, alveolar osteitis (AO) is a well-recognised post-surgical inflammatory disorder, which is easily diagnosed and simply recorded as a clinical outcome. AO is an inflammatory condition of failed healing, where the clot disintegrates and the lining of the alveolar bone becomes inflamed and painful. The incidence of AO following dental-oral surgical procedures is reported to be within the range of 5-40% (recent reports are consistently in the 22-30% range). This is similar to rates of delayed, difficult or painful healing reported for other surgical sites.

In 2012 both Tolstunov et al., *Brit. Dent. J.*, 2012, 213(12):597-601 and Yengopal et al., *Int. J. Oral Maxillofac. Surg.*, 2012, 41:1253-1264 reported on AO and current methods used to reduce its incidence. Neither report found evidence of effectiveness using chlorhexidine (0.2% solution or gel) or isotonic (normal) saline surgical site irrigation. Indeed, the most startling finding was that doing nothing was preferable to using any surgical site treatment, which is consistent with the understanding that AO is inflammatory in aetiology and not a response to infection.

Leg ulcers, particularly venous leg ulcers, are chronic wounds and inflammatory lesions, which often require lengthy treatment periods to heal or are difficult to heal at all. Venous ulcers are estimated to affect approximately one million people per year in Europe, and half a million people per year in the USA. The condition is particularly prevalent in older people, with the UK National Health Service estimating that 1 in 50 people over the age of 80 develop venous leg ulcers. The economic impact of hard to heal ulcers has been provided by Rippon et al., *Wounds*, UK, 2007, 3(2):58-69. Current recommended treatments are compression treatment or simple wound dressing, but there remains a need for a cheap, effective treatment, which can aid the healing of non-healing or difficult to heal leg ulcers.

Thus there continues to be a need for effective means to reduce the incidence rates of non-healing wounds and other inflammatory disorders following surgical intervention.

Recent reviews, studies, and definitive opinions from Cochrane library reviews and meta-analyses describe best practice in routine wound care and care for non-infected wounds, infected wounds and non-healing wounds (M. L. Rotter, "Special problems in hospital antisepsis," in *Russell, Hugo & Aycliffe's Principles and Practice of Disinfection, Preservation & Sterilisation*, 4th Ed. Blackwell Pub. 2008, Ch. 17: 540-562; Damour et al., Burns, 1992, 18(6):479-485; Fournel et al., Brit. J. Surg., 2010, 97:1603-1613; Brolmann et al., Brit. J. Surg., 2012, 99:1172-1183; Atiyeh et al., Int. Wound J., 2009, 6:420-430; Walter et al., Brit. J. Surg., 2012, 99:1185-1194; Thomas et al., J. Trauma, 2009, 66:82-91).

The present gold standard for the treatment with irrigation or cleansing of wounds is sterile saline or sterile water, usually in conjunction with antibiotics for the routine treatment of non-infected wounds. Pre-operative site preparations are used as topical antimicrobial agents before surgery. The use of antiseptics is not recommended in this context (Atiyeh et al., Int. Wound J. 2009, 6: 420-430; Fournel et al., Brit. J. Surg., 2010; Brolmann et al., Brit. J. Surg., 2012, 99:1172-1183; Leaper, Br. J. Surg., 2010, 97:1601-1602; Walter et al., Brit. J. Surg., 2012, 99:1185-1194).

Current best practice advises against the use of aqueous chlorine on wounds except for on infected wounds and where other treatment modalities have failed (Vissers et al., Biochem. J., 1999, 334:443-449; M. L. Rotter, "Special problems in hospital antisepsis," in Russell, Hugo & Aycliffe's Principles and Practice of Disinfection, Preservation & Sterilisation, 4th Ed. Blackwell Pub., 2008, Ch. 17:540-562; Damour et al., Burns, 1992, 18(6):479-485; Fournel et al.,Brit. J. Surg., 2010; Brolmann et al., Brit. J. Surg., 2012, 99:1172-1183; Walter et al., Brit. J. Surg., 2012, 99:1185-1194; and Atiyeh et al., Int. Wound J., 2009, 6:420-430).

Prior to the introduction of antibiotic chemotherapy, there was interest in the use of antiseptics for all wounds. Aqueous chlorine was assessed along with many other antiseptics, which were originally selected for their antimicrobial action. However, any interest in aqueous chlorine for use on all but infected, contaminated or chronic, non-healing wounds was ended by the seminal cytotoxicity study of Kozol et al., Arch. Surg., 1988, 123:420-423 and condemnation by Lineweaver et al., Arch. Surg., 1985, 120:267-270; and Leaper, Br. Med. J., 1992, 304:930-931). Subsequent investigations have shown that the benefits of the antimicrobial action of aqueous chlorine are outweighed by the harmful effects and cytotoxicity (Brennan et al., Brit. J. Surg., 1985, 72:780-782; (Vissers et al., Biochem. J., 1999, 334:443-449; Hideago et al., J. Burn Care Rehabil., 1991, 12:265-268; and Thomas et al., J. Trauma, 2009, 66:82-91; Coetzee et al., J. Burns, 2012, 38:529-533).

The rationale used by all advocates, whether current or historical, for the use of aqueous chlorine has been its antimicrobial action. Furthermore, all advice against the use of aqueous chlorine centres on its cytotoxicity.

Furthermore, while the use of aqueous chlorine in healthcare has been described in the context of the disinfection of surfaces and of contaminated wounds [see, for example, Bashford et al., Lancet, 1917, 2:595-597; Bunyan, Brit. Med. J., 1941, 4002-4007; and Century Pharmaceuticals Inc., Dakin's solutions product information and material safety data sheet, 2011, www dot dakins dot net slash index dot html], any such use has been limited by the prevailing knowledge that toxicity is a problem associated with the use of aqueous chlorine in the treatment of contaminated wounds.

Investigators have demonstrated that the toxicity seen and reported are such that only dilute solutions may be applied to live human or animal tissues without adverse effect. This reduction in concentration reduces antimicrobial efficacy, which is the only function of the aqueous chlorine solution in healthcare that has been reported to date.

Where the literature describes the use of aqueous chlorine solutions as anti-microbial and disinfectant agents, it is generally as a low pH solution to maximise the levels of hypochlorous acid, which is known to be an effective anti-microbial (see, for example, Chang, Journal of American Water Works Association, 1944, 36:1192-1207). Where the pH of the aqueous chlorine solution is not deliberately kept low, such formulations use a buffer to maintain a higher pH and maximise stability of the solution (see, for example, Estrela et al., J. Appl. Oral Sci., 2008, 16(6):364-368).

In recognition of the potential toxicity of hypochlorous acid alternative, less reactive antimicrobial agent alternatives have been developed to treat chronic non-healing and infected wounds, e.g., an N-Chloramine compound (NVC-422) developed by Novabay Pharmaceuticals. These alternative antimicrobial agents have been developed to address the cytotoxicity of aqueous chlorine, which is described as causing cellular damage and pain (see, for example, Gottardi et al., Antimicrob. Agents Chemother., 2013, 57(3):1107).

While the concept of using anti-microbial agents to wash out surgical sites has recently been discussed in the literature, the only antiseptic agents which were considered to be safe to use to wash out surgical sites and wounds were chlorhexidine 0.2% and povidone-iodine (see, for example, Khan et al., J. Tissue Viability, 2006, 16:6-10; Kozol et al., Arch. Surg., 1988, 123:420-423), refs. 28-30; and Leaper,Br. Med. J., 1992, 304:930-931).

In the seminal Kozol et al paper on the use of hypochlorite in a wound discussed earlier, it was concluded that, "there is no concentration at which it is safe to use hypochlorite on a wound." This statement has become the accepted knowledge of healthcare professionals and permeates wound-care policy.

The inventor of the present invention has now surprisingly found that that the aqueous hypochlorite solution according to the present invention is very beneficial in reducing the healing time and reducing the associated problems found with the healing of non-infected and uncontaminated surgical sites.

It has further been found that the aqueous hypochlorite solution of the present invention brings about the resolution of inflammatory disorders of the skin, mucosa and other surfaces, e.g., mouth ulcers, eczema, psoriasis, and leg ulcers, such as venous leg ulcers, where the cause is not microbial or infection.

Current treatment methods include skin moisturising with non-irritant emollients, compression treatment (in the case of leg ulcers), topical corticosteroid use, systemic corticosteroid medication (for severe acute episodes) and, in severe cases, systemic immunosuppressive therapy. All of these treatments have their limitations: emollients do not impact the inflammatory process and do not counter secondary infection; topical corticosteroids suppress cellular mediated immune responses, can compound the tendency to secondary infection and produce atrophy of the treated skin; and systemic immunosuppressive therapy has been linked to an increase in cancer incidence. As a result of these limitations many patients self-manage lesions over many months and often years.

It has further been found that use of an aqueous hypochlorite solution as a wound irrigant reduces the incidence of alveolar osteitis (AO) following dental-oral surgical procedures.

The beneficial effects of the solution of the present invention is particularly surprising because all literature to date has stated that the only safe use of hypochlorite solutions on wounds is to reduce a microbial bio-burden and treat infection.

It has surprisingly been found that a specific hypochlorite solution has a novel action on the inflammatory response and healing process associated with uncontaminated and non-infected surgical sites and wounds, as well as trauma sites and surface inflammatory lesions where there is no infection, e.g., recurrent oral ulcers, allergic dermatitis/eczema, psoriasis, and leg ulcers, such as venous leg ulcers.

SUMMARY OF THE INVENTION

Thus, in a first aspect of the present invention there is provided a dilute stabilised hypochlorite solution for use the prevention or treatment of an inflammatory response, condition or disease in a mammal, preferably a human.

As discussed in the background section earlier, in the seminal Kozol et al paper on the use of hypochlorite in a wound, it was concluded that "there is no concentration at which it is safe to use hypochlorite on a wound." This statement has become the accepted knowledge of healthcare professionals. Where it has been used, its use has been restricted solely to use as an antimicrobial but because of its toxicity the concentration required to function effectively as an antimicrobial is too low for it to be effective. The use of a dilute stabilised hypochlorite solution for use the prevention or treatment of an inflammatory response, condition or disease can thus be seen to be novel, surprising and to run totally contrary to the accepted advice of healthcare professionals in the treatments of wounds.

In a second aspect of the present invention there is provided a concentrated stabilised sodium hypochlorite solution to be diluted before use in the prevention or treatment of an inflammatory response, condition or disease in a mammal, preferably a human. Thus, the skilled practitioner is provided with the concentrated solution of the invention together with directions to dilute said solution to an appropriate concentration for the desired anti-inflammatory use. This concentration will either be known for a given condition or patient (based on prior knowledge of the condition and/or patient) or can be readily determined by simple trial and error by the practitioner of ordinary skill.

In a third aspect of the present invention there is provided a method for preventing or treating an inflammatory response, condition or disease in a mammal comprising administering an effective amount of a dilute stabilised hypochlorite solution to said mammal in need thereof. Preferably, said mammal is a human.

In a fourth aspect of the present invention there is provided use of a dilute stabilised hypochlorite solution in the preparation of a medicament for preventing or treating an inflammatory response, condition or disease in a mammal.

DETAILED DESCRIPTION OF THE INVENTION

The dilute stabilised hypochlorite solution for use in the prevention or treatment of an inflammatory response, condition or disease, is preferably dilute stabilised sodium hypochlorite solution. More preferably, said dilute stabilised sodium hypochlorite solution is in a concentration range of 0.005-0.2 wt %, yet more preferably 0.05-0.1 wt %.

The dilute stabilised hypochlorite solution for use in the prevention or treatment of an inflammatory response, condition or disease may further comprise sodium chloride, preferably in a concentration range of 0.5-1.5 wt %, more preferably in a concentration range of 0.8-1.0 wt %.

The dilute stabilised hypochlorite solution for use in the prevention or treatment of an inflammatory response, condition or disease may be a dilute stabilised sodium hypochlorite solution, which is buffered to a pH of from 5-11, preferably 6-8. The buffer may be any suitable buffer conventionally used in the pharmaceutical field, and is preferably selected from the group consisting of a phosphate/phosphoric acid buffer, a borate/boric acid buffer, and a citrate/citric acid buffer.

The dilute stabilised hypochlorite solution of the present invention may be used in the prevention or treatment of an inflammatory response in an uncontaminated or non-infected surgical site, wounds, trauma sites or surface inflammatory lesions where there is no infection, preferably a non-healing wound or an oral wound. Infection in the context of the present invention has its ordinary meaning as would be understood by the person of ordinary skill in this field, e.g., the invasion and multiplication of microorganisms such as bacteria, viruses, and parasites that are not normally present within the body or at the site of the infection. Infection in this context can be either primary or opportunistic.

The dilute stabilised hypochlorite solution of the present invention may also be used in the prevention or treatment surface inflammatory lesions, an inflammatory skin condition where there is no infection, and also in the treatment of inflammatory pain, rheumatoid diseases and Alzheimer's degenerative disorders of the nervous system e.g., mouth ulcers, eczema, psoriasis, leg ulcers, venous ulcers, venous leg ulcers, allergic dermatitis, contact inflammatory dermatitis, stasis dermatitis, seborrheic dermatitis, inflammatory nociceptive pain, inflammatory neuropathic pain, inflammatory stomatitis, rheumatoid arthritis, Alzheimer's disease, rosacea or lupus, preferably eczema, psoriasis, leg ulcers, venous ulcers or venous leg ulcers.

Eczema is an itching (pruritic) inflammatory condition of the skin, which can occur in response to known irritants, allergens or stresses. The cellular and histological changes associated with its pathology have been studied extensively. A typical sequence of inflammatory changes occurs at the site of inflammation, and the pathogenesis includes cellular action (e.g., mast cell degeneration) and release of inflammatory mediators (e.g., histamine and cytokines).

Psoriasis is an immune-mediated disease that affects the skin. It is typically a lifelong condition. There is currently no cure, but various treatments can help to control the symptoms. Psoriasis occurs when the immune system mistakes a normal skin cell for a pathogen, and sends out faulty signals that cause overproduction of new skin cells. The cause of psoriasis is not fully understood. There are two main hypotheses about the process that occurs in the development of the disease. The first considers psoriasis as primarily a disorder of excessive growth and reproduction of skin cells. The problem is simply seen as a fault of the epidermis and its keratinocytes. The second hypothesis sees the disease as being an immune-mediated disorder in which the excessive reproduction of skin cells is secondary to factors produced by the immune system. T cells (which normally help protect the body against infection) become active, migrate to the dermis and trigger the release of cytokines (tumor necrosis factor-alpha TNFα, in particular), which cause inflammation and the rapid production of skin cells. It is not known what initiates the activation of the T cells. The immune-mediated model of psoriasis has been supported by the observation that immunosuppressant medications can clear psoriasis plaques.

Leg ulcers are long lasting, chronic wounds and inflammatory lesions on the leg or foot. Venous leg ulcers are the most common kind of leg ulcer, and are particularly prevalent in older people. There are various causes of leg ulcers, but risk factors include obesity, deep vein thrombosis, varicose veins, diabetes, peripheral arterial disease and simply increasing age. Treatment includes compression treatment, such as by application of a compression bandage or graduated elastic medical compression stocking, and by simple dressing of the wound. Both require frequent monitoring and prolonged treatment periods, and can be ineffective in the treatment of hard to heal or chronic ulcers.

Without wishing to be bound by theory, it is thought that the dilute stabilised hypochlorite solution of the present invention acts on the known initiators, mediators and regulators of inflammation in surgical sites and surface inflammatory lesions. The solution of the invention is thought to inhibit the release of inflammatory agents (e.g., cytokines and chemokines) from blood platelets, but does not prevent the platelets from aggregating. It is thought that the solution also attenuates the effect of cytokines, chemokines and other inflammatory mediators.

The dilute stabilised hypochlorite solution has a beneficial effect within specific concentration ranges, the exact identity of which will vary from condition to condition and patient to patient. These ranges are either disclosed in the present application or will be easily determined by the practitioner of ordinary skill in this field by simple trial and error on the basis of the knowledge of the present invention herein and the condition that is being presented.

Beneficial effects for the prevention or treatment of an inflammatory response in an uncontaminated or non-infected surgical site, wounds, burns, trauma sites and for inflammatory skin conditions are particularly noticeable where the patient is treated with a dilute stabilised solution which has a concentration range of 0.005-0.2 wt %, preferably 0.05-0.1 wt %, more preferably 0.005-0.1 wt. % sodium hypochlorite; sodium chloride in a concentration range of 0.5-1.5 wt %, preferably in a concentration range of 0.8-1.0 wt %; wherein said solution is buffered to a pH of from 5-10, preferably 6-8. For example, a dilute stabilised solution comprising 0.85% sodium chloride and 0.05% sodium hypochlorite w/w has been found to be very beneficial in preventing and treating an inflammatory response, condition or disease in a mammal, preferably a human, e.g., in uncontaminated or non-infected surgical sites, wounds, trauma sites or surface inflammatory lesions where there is no infection and in prevention and treatment of inflammatory skin conditions. This range of concentrations has previously been considered in the medical literature to be toxic. The hypochlorite should be very pure, e.g., ideally it should be generated electrolytically to ensure its purity as well as its safety and effectiveness.

In a preferred embodiment of the present invention, the dilute stabilised hypochlorite solution for use in the prevention or treatment of an inflammatory response, condition or disease according to the present invention may further comprise an indicator to show the activity of the dilute hypochlorite solution, in other words, the indicator shows the dilute hypochlorite solution is fresh and active. The indicator is not the active ingredient of the dilute hypochlorite solution. The indicator preferably degrades over time when mixed with the dilute hypochlorite solution. In other words, the indicator preferably does not degrade over time when mixed with either neat dilutant or neat hypochlorite. The indicator may comprise a first component which shows the dilute hypochlorite solution is fresh and active and a second component which degrades the first component.

The indicator (e.g., first component) may be a dye or a flavour or combination thereof (e.g., in a mouthwash). The indicator preferably produces a noticeable change over time to a user of the dilute hypochlorite solution. For example, for a dye, there is either a significant colour change or the solution becomes colourless. For a flavour, there is a noticeable degradation of the flavouring such that the solution becomes unpalatable. Since the resultant solution is most effective, if diluted immediately prior to use, the noticeable change may occur within a time frame of 45 minutes to 1 hour. In this time frame, the noticeable change occurs prior to the loss of therapeutic action of dilute hypochlorite solution.

The dye may be a dye such as those which are routinely used in surgical procedures with no adverse effects. Examples of suitable dyes include azatioxin, basic blue (nil blue sulphate), bismarck brown, basic red (rhodamine 6G), bengal red, brilliant crysyl blue, eosin, fluorescein, gentian violet, indocyanine green, janus green, methylene green, methylene blue, neutral red, trypan blue, and trypan red. The predetermined amount of dye is preferably low enough to prevent interaction with active components but great enough so that the dye colour is visible within the dilute hypochlorite solution.

The indicator may be organic or inorganic, biocompatible, non-toxic and pharmaceutically acceptable.

In one embodiment of the invention, the indicator (preferably a dye) may indicate the strength or dilution of the dilute stabilised hypochlorite solution for use in the prevention or treatment of an inflammatory response, condition or disease. For example, if the hypochlorite is diluted by ten (1 part hypochlorite in 10 parts of water) then the indicator dye would be blue. If the hypochlorite is diluted by 20 (1 part of hypochlorite in 20 parts of water) the indicator would be green. If the hypochlorite is diluted by 30 (1 part hypochlorite in 30 parts of water) then the hypochlorite dye would be orange. If the hypochlorite is diluted by 40 (1 part hypochlorite in 40 of water) then the indicator dye would be red. In such an aspect, the hypochlorite dye may preferably be packaged with the specific dilution.

In another embodiment of the present invention, the indicator may also show that the hypochlorite for use in the prevention or treatment of an inflammatory response, condition or disease is at the correct dilution.

In yet another embodiment of the present invention, the indicator may be an organic or inorganic dye which can be degraded by the innate oxidative capacity chemical action of the dilute stabilised hypochlorite solution for use in the prevention or treatment of an inflammatory response, condition or disease.

The indicator may suffer a diminishment of intensity over a period of 1 hour. This indicates the activity of the dilute stabilised hypochlorite solution is not sufficiently reliable to produce the clinical action desired.

In another preferred embodiment, the indicator is selected so that it degrades and shows a change in property over the same period in which the activity of the chosen dilution of the stabilised hypochlorite degrades. For example, one dye might change from coloured to colourless over 30 minutes, while another might make this change over 1 hour while another might take 2 hours.

Where the indicator is a dye, the colour degradation of the indicator dye may be used as an indicator of the reduction in activity of the dilute stabilised hypochlorite solution. The intensity of the colour can be measured by comparison to a set colour charts or with a calibrated optical measuring device to indicate hypochlorite activity.

The dilute hypochlorite solution can have an indicator such as a dye added after its dilution to indicate continued activity. For example, the dilute hypochlorite (e.g., Milton's 2 wt % sodium hypochlorite or Milton's 1 wt % sodium hypochlorite in 16.5 wt % sodium chloride solution diluted with water) may have an indicator dye added to it for the first time after the dilution or additional indicator dye may be added to indicate continued activity.

In one embodiment of the invention, the indicator may be an indicator dye which is an unstable compound which spontaneously degrades over a period of time (preferably from 30 minutes to 2 hours, e.g., over 30 minutes, 45 minutes, 1 hour or 2 hours). In this embodiment, the indicator is preferably formed at the time of dilution of the disinfectant by adding two separate components together in order to generate the indicator dye. Once generated it is then added to the dilute hypochlorite solution, after which the indicator dye "degrades" from exhibiting colour (e.g., red, blue or green) to being colourless.

Where an indicator is present and the indicator is a dye, a further advantage is that the dilute stabilised hypochlorite solution can be seen to be present at the treatment site. It can therefore be visually confirmed that the dilute hypochlorite solution is being delivered to the intended area and that it is being applied or circulated throughout the entire treatment site. Thus a blockage or incomplete circulation can be detected and the dilute hypochlorite solution can be reapplied as necessary. This may be particularly advantageous where the inflammatory response, condition or disease is an ulcer, particularly a venous ulcer, e.g., a venous leg ulcer.

As explained earlier, in a second aspect of the present invention there is provided a concentrated hypochlorite solution to be diluted before use in the prevention or treatment of an inflammatory response, condition or disease in a mammal, preferably a human. Preferably, the concentrated hypochlorite solution to be diluted before use is a concentrated stabilised sodium hypochlorite solution. The concentrated stabilised hypochlorite solution when diluted to the appropriate dilution to give a dilute stabilised hypochlorite solution may be used in the prevention or treatment of an inflammatory response, condition or disease in a mammal, preferably a human. These are as discussed and exemplified earlier.

The concentration of hypochlorite for use in accordance with the second aspect of the present invention may be in the range of 0.5 to 3 wt %. Furthermore, the concentrated hypochlorite solution may be buffered to a pH of from 9-15, preferably 11-13.

The concentrated hypochlorite solution may be a stabilised sodium hypochlorite solution at 1% or 2% sodium hypochlorite, e.g., a disinfectant known as "Milton's Solution" comprising sodium chloride. The dilute hypochlorite solution may be a 2.5%-10% solution of Milton's solution diluted in water where the disinfectant solution is 2% sodium hypochlorite. The sodium chloride in said solution is typically at a concentration of 16.5%. Thus, the ratio by volume of the hypochlorite solution to water may be in the range of between 1 to 10 to 1 to 40. Alternatively, the dilute hypochlorite solution may be a 5% to 20% solution of Milton's solution diluted in water where the disinfectant solution is 1% sodium hypochlorite. In this case, the ratio by volume of the hypochlorite solution to water may be in the range of between 1 to 5 to 1 to 20.

In both cases, the predetermined amount of water and the predetermined amount of sodium hypochlorite solution may be such that the dilute disinfectant solution may be a stabilised sodium hypochlorite solution where the sodium hypochlorite is in a concentration range of 0.025%-0.2%, preferably 0.05%-0.1%. The action of the sodium hypochlorite solution can provide stabilisation of the dilute disinfectant solution.

In the third aspect of the present invention as described above, there is provided a method for preventing or treating an inflammatory response, condition or disease in a mammal comprising administering an effective amount of a dilute stabilised hypochlorite solution to said mammal in need thereof. Preferably, said mammal is a human. In preventing or treating an inflammatory response, condition or disease in a mammal, preferably a human, the inflammatory responses, conditions or diseases, which may be treated and the dilute hypochlorite solutions suitable are as discussed and exemplified earlier in relation to the first aspect of the invention.

In the present invention, the dilute stabilised hypochlorite solution may be administered for use as an irrigating solution for surgical sites, burns or wounds. Alternatives include:
1. A solution to be applied over surgical sites before, during or after surgical procedures, e.g., via a bottle or drip-bag.
2. A solution to be applied to burns or wounds via a constant stream or via a bag sealed at the edges to retain the solution over the wound. The solution is to be changed every one to six hours for freshness.
3. A solution to be used as a mouth rinse or after oral or dental or surgical procedures.

For inflammatory skin conditions, means for the constant application of hypochlorite solution to the affected area may be applied. These include:
1. A reservoir such as paper or gauze soaked in diluted stabilised hypochlorite solution and held in place over the affected area by a suitable means such as an elasticated bandage. This should be a number of times per day (e.g., 3 to 4 times) to ensure that the hypochlorite solution remains fresh, active and that the reservoir has not dried up.
2. Irrigation of the affected area with diluted stabilised hypochlorite solution followed by the procedure in 1 above.
3. Use of a carrier which is preferably inert and without interaction with the dilute stabilised hypochlorite solution In the fourth aspect of the present invention as defined above, there is provided use of a dilute stabilised hypochlorite solution in the preparation of a medicament for preventing or treating an inflammatory response, condition or disease in a mammal, preferably a human.

The dilute stabilised hypochlorite solution for use in the prevention or treatment of an inflammatory response, condition or disease in a mammal, preferably a human according to the present invention is preferably freshly prepared and administered, wherein said dilute stabilised hypochlorite solution is administered using a portable device for mixing a dilute hypochlorite solution comprising:
  a disinfectant reservoir holding hypochlorite solution,
  a chamber which is connected to said hypochlorite reservoir and which is for holding a predetermined amount of dilutant, and
  hypochlorite discharging means for discharging a predetermined amount of said hypochlorite solution from said first reservoir to be mixed with said predetermined amount of dilutant, whereby said device provides the dilute hypochlorite solution at a fixed dilution determined by the ratio of the predetermined amount of said hypochlorite solution to the predetermined amount of dilutant.

The concentration of the hypochlorite solution in the disinfectant reservoir may be from 0.5 to 3 wt %, preferably 1 wt % or 2 wt %.

The portable device for mixing a dilute hypochlorite solution may be in the form of a drip bag or a bottle. The portable device may be configured to deliver the dilute disinfectant solution to wounds. In one embodiment, the chamber of the portable device is attached around the wound to retain the dilute disinfectant solution over the wound.

A device suitable for preparing a dilute stabilised hypochlorite solution for use in the present invention is described in WO-A-2011/128862.

Various embodiments and optional features are described above. It will be appreciated that these embodiments and features can be combined in all viable permutations.

The present invention may be further understood by reference to the following, non-limiting examples.

EXAMPLES

Example 1

A Caucasian north European male in $5^{th}$ decade has suffered atopic eczema since childhood. The patient presented with long-standing, chronic skin lesions on the anterior skin surface of the lower leg on the right and left side. The lesions had been present for 24 months and had proven refractory to treatment with topical hydrocortisone (1%) and emollient cream, with the lesions recurring despite temporary resolution.

Treatment comprised application of a combination of the application of dilute stabilised aqueous sodium hypochlorite solution in saline (NaOCl: 0.05 wt %, NaCl: 0.85 wt %; pH 10) to the surface of the lesion alternating with the use of a gold standard emollient (Diprobase™, a cream comprising a mixture of liquid paraffin, white soft paraffin, cetomacrogol and cetostearyl alcohol). A paper square solution soaked in the dilute stabilised aqueous sodium hypochlorite solution in saline was applied against the lesion on the left leg and held in place with a Tubigrip™ elastic bandage. To prevent drying, the solution was replenished six times a day and worn for a 12-24 hour period. For the following three days, the emollient was applied twice daily. On every fourth day the cycle was repeated.

As a negative control, symmetrical lesions on the patient's right leg were treated only with isotonic saline solution in an identical way followed by emollient as on the left leg.

After two weeks of treatment the patient reported total elimination of pruritis during the application of dilute stabilised aqueous sodium hypochlorite solution in saline and a progressive recovery to normal skin on the left leg, with normal colour and hair coverage, whilst the skin on the right leg remained eczematous, inflamed and pruritic.

As a cross-over control, the lesions on the patient's right leg (i.e., the original control lesions) were, subsequently, treated with dilute buffered aqueous sodium hypochlorite solution in saline and emollient as described above.

The symptoms of itching of the previous control site on the right leg resolved themselves within 60 minutes of placing the aqueous chlorine solution in saline towel over the lesion, and the lesion was resolved in a similar manner to the lesions on the patient's left leg.

This Example demonstrates the anti-inflammatory action of the dilute stabilised aqueous sodium hypochlorite solution in saline where the lesion is not a surgical site with haemostasis and where there is no infection. It was compared to isotonic saline as a control with identical soaking and emollient use.

Example 2

The same patient as in Example 1 developed a new and acute atopic eczema lesion on the dorsal surface of the right foot. The lesion developed over a period of 6 hours beginning with severe itching and formation of broken skin with exudate production.

The lesion was treated immediately with dilute stabilised aqueous sodium hypochlorite solution in saline, by soaking a towel with the solution and holding it in place with a Tubigrip™ elastic bandage. Treatment continued as described in Example 1, with dilute stabilised aqueous sodium hypochlorite solution in saline and the Diprobase™ emollient.

Over the course of four days the lesion resolved totally, with itching stopping within 12-24 hours. The inflammatory area was identifiable due to the redness of the skin, which also became dry. The lesion then reduced in redness and dryness and became identical with the adjacent unaffected skin.

Example 3

The same patient as described in Examples 1 and 2 above had new lesions on the dorsal surface of the left foot.

These lesions were treated with a more concentrated dilute stabilised aqueous sodium hypochlorite solution in saline (0.075 wt % NaOCl, i.e., 1.5 times more concentrated than the solution used in Examples 1 and 2). As before, the concentration of the aqueous sodium chloride (NaCl) was greater than 0.45 wt % and less than 0.85 wt %. Treatment was according to the protocol described in Examples 1 and 2.

In the initial 2 hours of treatment, there was a reduction in itching, but no reduction in erythema (redness). However, over 3-6 hours the lesion on the left foot dorsal surface enlarged and itching became more severe.

This increase in lesion size and itching severity was reversed within 6 hours of treatment with a 0.05 wt % NaOCl dilute stabilised sodium hypochlorite solution in saline, i.e., the solution used in Examples 1 and 2.

This indicates that the beneficial effects of the dilute stabilised sodium hypochlorite solution in saline are dependent on the concentration of sodium hypochlorite used, with increased concentrations causing a reversible increase in the size of lesions and severity of itching.

Higher concentrations of sodium hypochlorite have been seen to cause irritation rather than resolution of eczema lesions, and thus the concentrations of the dilute stabilised sodium hypochlorite solutions used in the treatments of the present invention must be carefully controlled, although the precise concentration that is suitable will vary depending upon the condition to be treated and the patient that is being treated.

Example 4

Another patient (Patient B) was a white Caucasian male, in his $7^{th}$ decade. He was a long-standing eczema sufferer. He had several lesions, which to him were defined by the cycle of itch-scratch-bleed-scab. The eczema had been resistant to treatment over several decades.

When the patient was presented to us, he had lesions on his right foot, right upper leg lateral aspect and on the right lower leg below the knee, anterior surface. All the lesions were notable for their slightly raised surface. Similar lesions were also present on the left leg.

For the treatment, as previously described a simple paper towel was saturated with dilute, stabilised aqueous sodium hypochlorite solution (NaOCl: 0.05 wt %, NaCl: 0.85 wt %; pH 7-8) and applied to the area using a Tubigrip™ elastic bandage. The saturated towel was replaced every 3-4 hours. The left leg and foot was left untreated as a control.

For all treated areas, it was found that itching was totally resolved within 1 hour of application of the dilute hypochlorite solution. Over 48 hours the lesions made rapid progression towards resolution. Itching stopped and the skin began to heal over. The bulk of hyperkeratinised material became less thick and noticeable. On the other hand, the lesions on the control left leg remained unchanged. After 6 days treatment, there was further resolution and the lesions had remained free from itching which improved even further after 8 days with the lesions very visually improved. At this point, the dilute, stabilised aqueous sodium hypochlorite solution treatment was then applied to the control lesions on the left leg which had remained largely unchanged during the period of the experiment. We found that this proceeded to resolve in line with the other sites on the original test right leg.

Example 5

Progress in Patient B became intermittent. It was found that compliance with his treatment regime had become poor. As a consequence, treatment was re-started with the application for 24 hours of dilute, stabilised aqueous sodium hypochlorite solution (NaOCl: 0.05 wt %, NaCl: 0.85 wt %; pH 7-8) as in Example 4 above for 24 hours together with Diprobase™ for 12 hours. The lesions went on to resolve rapidly over the next 5 days. The patient then stopped the treatment with the solution, before complete resolution and continued only with Diprobase. The lesions developed again. After re-commencing the soaking of the lesions with the said solution the lesions progressed to resolution. Most valuable to the patient was the absence of itching. Furthermore, the eczema lesion on the right foot in which secondary fungal infection had occurred also resolved. This demonstrates that the dilute, stabilised aqueous sodium hypochlorite solution must be applied continuously for effective anti-inflammatory treatment.

Example 6

Radiotherapy produces an obliteration of small blood vessels (endarteritis obliterans) in the irradiated area. As a result tissue in the irradiated area can break down spontaneously and wounds such as fistulas are very difficult to heal. Such wounds commonly persist for months or years.

A patient suffered a fistula formation between the colon and supra-pubic region of the abdomen as a two year post external-beam radiotherapy late complication. On presentation to the hospital, faecal matter was discharging externally. This type of wound is unusual and particularly severe.

Following a colostomy to move the stoma outside the irradiated region, no faecal matter was passing to the fistula region. After surgery the fistula was cleaned to be free of infection and left open. Cleaning of the wound continued for 14 days following the initial surgery, with no signs of infection. However, the wound did not progress, with the wound site being inflamed and covered with a necrotic slough with bowel secretions leaking via the fistula from the lower and left-side edges, despite there being no infection present.

In an attempt to address this inflammatory reaction, we administered dilute stabilised sodium hypochlorite solution to the wound area. Treatment was conducted with dilute stabilised sodium hypochlorite solution in saline (NaOCl 0.05 wt %, NaCl 0.5 wt %, pH 7-8) by dripping of the solution into the wound area to soak it, and by laying gauzes soaked in the solution over the wound. Treatment was for 90 minutes, twice daily.

The healing of the wound progressed as follows:
Wound surface inflammation was contained and the surface appearance of the wound improved with reduction then elimination of slough/exudate.
The connective tissue within the wound was switched from inflammatory mode to healing such that the tissue reverted to its correct type. Out of the granulating tissue arose lining of colon, smooth muscle, dense fibrous connective tissue, peritoneum, striated muscle, deep fascia, fat, superficial fascia and skin.
The size and extent of the wound reduced inward from the edges and there are signs that islands of epithelium are forming within the centre of the wound.
The fistula had closed by the 19$^{th}$ day of treatment, and was now a wound. Normal hair growth in the skin at the edges of the wound had commenced. After 39 days, edges of rapid re-epithelialisation and signs of islands of keratinising (white) epithelium were observed. After 67 days, the skin wound was dry and could be managed simply with a dry dressing. After 102 days, the skin wound was almost completely healed.

It can thus be seen that washing and dressing with a dilute stabilised sodium hypochlorite solution in saline enabled progress of a previously non-progressing fistula wound, with the wound site being inflamed and covered with a necrotic slough with bowel secretions leaking via the fistula from the lower and left-side edges to a stage where it had almost completely healed in the space of only 102 days. This emphasises the extent to which the dilute stabilised sodium hypochlorite solution of the present invention may be used in reducing the healing time and reducing the associated problems found with the healing of non-infected and uncontaminated surgical sites.

Example 7

Dilute stabilised sodium hypochlorite solution in saline (NaOCl 0.05 wt %, NaCl 0.5 wt %, pH 7-8) was used in the management of a homogeneous set of oral surgical procedures. The study group comprised 377 cases. Details of the individual patient, site and nature of the surgery, and the clinical outcomes were recorded.

As a control group, an identical homogeneous set of oral surgical procedures were performed where no solution was used. The control group comprised 107 cases. The study group and control group were each operated on by separate clinicians, who had similar levels training, experience and competence in performing the oral surgery procedures.

No pre- or post-operative antibiotics were prescribed unless indicated at the post-surgical review because alveolar osteitis (AO) had developed.

All consecutive patients where dental extractions were indicated were included in the study. No medical conditions excluded patients from the study; the study group included a number of patients who would usually be excluded due to conditions where healing is often compromised, e.g., diabetics, post-splenectomy, smokers. The surgical procedures were homogeneous as is typical for out-patient dental extractions.

Patients attended via routine out-patient appointment following a consultation. Patients had not been starved and had taken any routine medications as prescribed by their general medical practitioner.

Anaesthesia/analgesia was achieved via standard approaches using standard local anaesthetic solutions licensed in the UK. The dental extractions were carried out using standard techniques as described in oral surgery textbooks and were applied homogeneously throughout the study and control groups. Haemostasis was achieved via local pressure over the socket with cotton wool rolls and biting pressure. Occasionally 3-0 braided silk sutures were placed.

Within the study group, once the tooth was extracted the wound/socket was irrigated with dilute stabilised sodium hypochlorite solution in saline using 10-20 mL of the solution via a syringe and a blunt ended needle (endodontic irrigation needle). Dental cotton rolls were soaked in the same solution and the patient applied biting pressure onto the wound via the soaked cotton rolls. The patient was instructed to rinse four times a day with dilute stabilised sodium hypochlorite solution in saline for five to ten days. Compliance with mouth rinse use was not monitored. All of the study group were reviewed a week after the surgical procedure.

Within the control group, all protocols were identical to the study group except that the wound was not irrigated at all and the cotton rolls were either dry or soaked in saline solution. Patients were instructed to rinse four times a day with warm salt-water mouth rinse or corsodyl (0.2% chlorhexidine antimicrobial solution) mouth rinse for five days. This post-surgery rinse procedure is the current gold standard of care. Compliance with mouth rinse use was not monitored.

No routine follow-up was arranged for the control group. If the patient did not return due to pain or problematic healing within two weeks, a successful outcome was recorded. All patients were subsequently reviewed. If the patient returned within 14 days with increasing pain and unsuccessful healing it was classified as a healing complication and recorded as complicated healing/wound infection.

The results are shown in Table 1 below.

TABLE 1

| Group | Total subjects | Uneventful Healing | Complication with healing | % Complication | % Problem-free healing |
|---|---|---|---|---|---|
| Study | 377 | 373 | 4 | 1.06 | 98.9 |
| Control | 107 | 77 | 30 | 28.0 | 72.0 |

As can be seen from the results in Table 1, it is clear that the use of dilute stabilised sodium hypochlorite solution in saline as a routine adjunct in this series of oral surgical procedures resulted in a dramatic improvement in healing outcomes, with an over twenty-fold reduction in the incidence of healing complications from 28% to 1%. The 28% incidence rate in the control group is consistent with literature values obtained by other investigators.

Additionally, patients who had the dilute stabilised sodium hypochlorite solution in saline used to irrigate the surgical site and also as a mouth rinse reported perceiving no or very little pain. Furthermore, several patients reported that if any soreness developed, use of the mouth rinse eliminated it. This is consistent with a reduction in inflammation at the uninfected surgical site.

Other patients (outside of either the study or control groups) who presented with failure to heal over six weeks and significant pain following oral surgery also reported immediate benefits with resumed healing following simple irrigation of the site with dilute stabilised sodium hypochlorite solution in saline.

Example 8

A 90 year old patient suffering from Alzheimer's disease presented a leg ulcer which had not healed over a six month period despite trying conventional treatments of pressure bandages and anti-microbial dressings. Furthermore, the situation was complicated because she removed the dressings during the day having forgotten why they were placed there. The ulcer often bled due to an anticoagulant therapy (warfarin) that she was taking for atrial valve incompetence. The leg ulcer had relapsed after previously successful treatment, the resolution having been short lived.

The treatment of this example comprised washing the leg ulcer for 10 minutes with a freshly constituted solution of sodium hypochlorite in saline (NaOCl: 0.05 wt %, NaCl: 0.85 wt %; pH 7-8) at twice daily dressing changes. The dressing itself was placed with a gauze square soaked with the same freshly constituted solution of sodium hypochlorite in saline.

The washing and re-dressing was repeated twice daily and checked weekly for progress. It was found that the size of the ulcerated area diminished over the first 7 to 10 days and the surrounding inflamed and erythematous area was also reduced. Over a period of 3 weeks, the lesion diminished from its original dimension to less than 10% of its original surface area. Over the next 3 weeks it fully resolved and it has not recurred in the 18 months since.

Chronic leg (or venous) ulcers are a significant problem for the elderly and individuals with healing or vascular problems (e.g., diabetics). Treatment can extend over a very long period and these ulcers can remain unresolved for years. The dilute stable hypochlorite solution of the present invention provides a local anti-inflammatory agent which is an effective agent in treating this disorder. Furthermore, the treatment is simple, relying only on freshly constituted dilute sodium hypochlorite in saline used both as a wash and applied to the lesion via, for example, a soaked gauze.

The invention claimed is:

1. A method for treating an inflammatory response in burns in a mammal comprising administering an effective amount of a dilute stabilized hypochlorite solution to said mammal in need thereof, wherein the dilute hypochlorite solution consists of:
   (i) water; sodium hypochlorite in a concentration range of 0.05-0.1 wt %; and sodium chloride in a concentration range of 0.5-1.5 wt %; or,
   (ii) water; sodium hypochlorite in a concentration range of 0.05-0.1 wt %; sodium chloride in a concentration range of 0.5-1.5 wt %; and an indicator.

2. The method according to claim 1, wherein the indicator shows that the dilute stabilized hypochlorite solution is present at the treatment site.

3. The method according to claim 1, wherein the indicator provides visual confirmation that the dilute stabilized hypochlorite solution is present at the treatment site, wherein said indicator is a dye.

4. The method according to claim 1, wherein the indicator shows that the dilute stabilized hypochlorite solution is applied or circulated throughout the entire treatment site.

5. The method according to claim 1, wherein the indicator provides visual confirmation that the dilute stabilized hypochlorite solution is applied or circulated throughout the entire treatment site, wherein said indicator is a dye.

6. The method according to claim 1, wherein the indicator shows that the dilute stabilized sodium hypochlorite solution is fresh and active.

7. The method according to claim 1, wherein the indicator shows that the dilute stabilized sodium hypochlorite solution is fresh and active, wherein said indicator is a dye or a flavor or a combination thereof.

8. The method according to claim 1, wherein the indicator shows that the dilute stabilized sodium hypochlorite solution is fresh and active, wherein said indicator also shows that the sodium hypochlorite is at the correct dilution.

9. The method according to claim 1, wherein the mammal is a human.

10. The method according to claim 1, wherein said sodium chloride is in a concentration range of 0.8-1.0 wt %.

11. The method according to claim 1, wherein said dilute stabilized sodium hypochlorite solution is administered for use as an irrigating solution.

12. The method according to claim 1, wherein said dilute stabilized sodium hypochlorite solution is adapted for application applied to burns or wounds via a constant stream or via a bag sealed at the edges to retain the solution over the burn.

13. A method for treating an inflammatory response in uncontaminated or non-infected burns in a mammal, the method comprising administering an effective amount of a dilute stabilized hypochlorite solution to said mammal in need thereof, wherein the dilute hypochlorite solution consists of:
 (i) water; sodium hypochlorite in a concentration range of 0.005-0.2 wt %; and sodium chloride in a concentration range of 0.5-1.5 wt %; or,
 (ii) water; sodium hypochlorite in a concentration range of 0.005-0.2 wt %; sodium chloride in a concentration range of 0.5-1.5 wt %; and an indicator.

14. A method according to claim 13, wherein said sodium hypochlorite is in a concentration range of 0.05-0.1 wt %.

* * * * *